United States Patent [19]
Shene

[11] Patent Number: 4,606,331
[45] Date of Patent: Aug. 19, 1986

[54] ELECTRODE FOR FIBER OPTIC SCOPES

[75] Inventor: William R. Shene, Plattsburgh, N.Y.

[73] Assignee: Monghan Medical Corporation, Plattsburgh, N.Y.

[21] Appl. No.: 772,039

[22] Filed: Sep. 3, 1985

[51] Int. Cl.⁴ .......................... A61B 17/36; A61B 1/06
[52] U.S. Cl. ........................................ 128/24.1; 128/4; 128/303.15
[58] Field of Search ................ 128/4, 6, 24.1, 303.13, 128/303.14, 303.15, 303.16, 303.17, 303.18

[56] References Cited

U.S. PATENT DOCUMENTS

| 2,275,167 | 3/1942 | Bierman | 128/303.17 |
|---|---|---|---|
| 2,828,747 | 4/1958 | August | 128/303.14 |
| 3,100,482 | 8/1963 | Hett | 128/6 |
| 3,294,085 | 12/1966 | Wallace | 128/6 |
| 3,670,721 | 6/1972 | Fukami | 128/6 |
| 3,884,237 | 5/1975 | O'Malley | 128/303.14 |
| 3,961,621 | 6/1976 | Northeved | 128/6 |
| 4,176,662 | 12/1979 | Frazer | 128/6 |

FOREIGN PATENT DOCUMENTS

| 1466248 | 12/1966 | France | 128/4 |
|---|---|---|---|
| 100517 | 2/1984 | Japan | 128/4 |
| 607292 | 8/1948 | United Kingdom | 128/303.13 |

Primary Examiner—Clyde I. Coughenour

[57] ABSTRACT

An electrode for use in fiber optic scopes has a connecting end and a discharge end and includes an elongated flexible center conductor and an inner insulation sleeve extending along and covering the conductor. An outer insulation sleeve extends along and covers the inner insulation sleeve and leaves a gap therebetween to define an irrigant conduit between the inner and outer insulation sleeves. A metallic sleeve extends along the irrigant conduit, the metallic sleeve being of a woven braided material whereby to permit passage of the irrigant through the irrigant conduit. Irrigant input means are in communication with the irrigant conduit. Adjacent the discharge end of the electrode is a balloon for centering the electrode in a duct.

12 Claims, 4 Drawing Figures

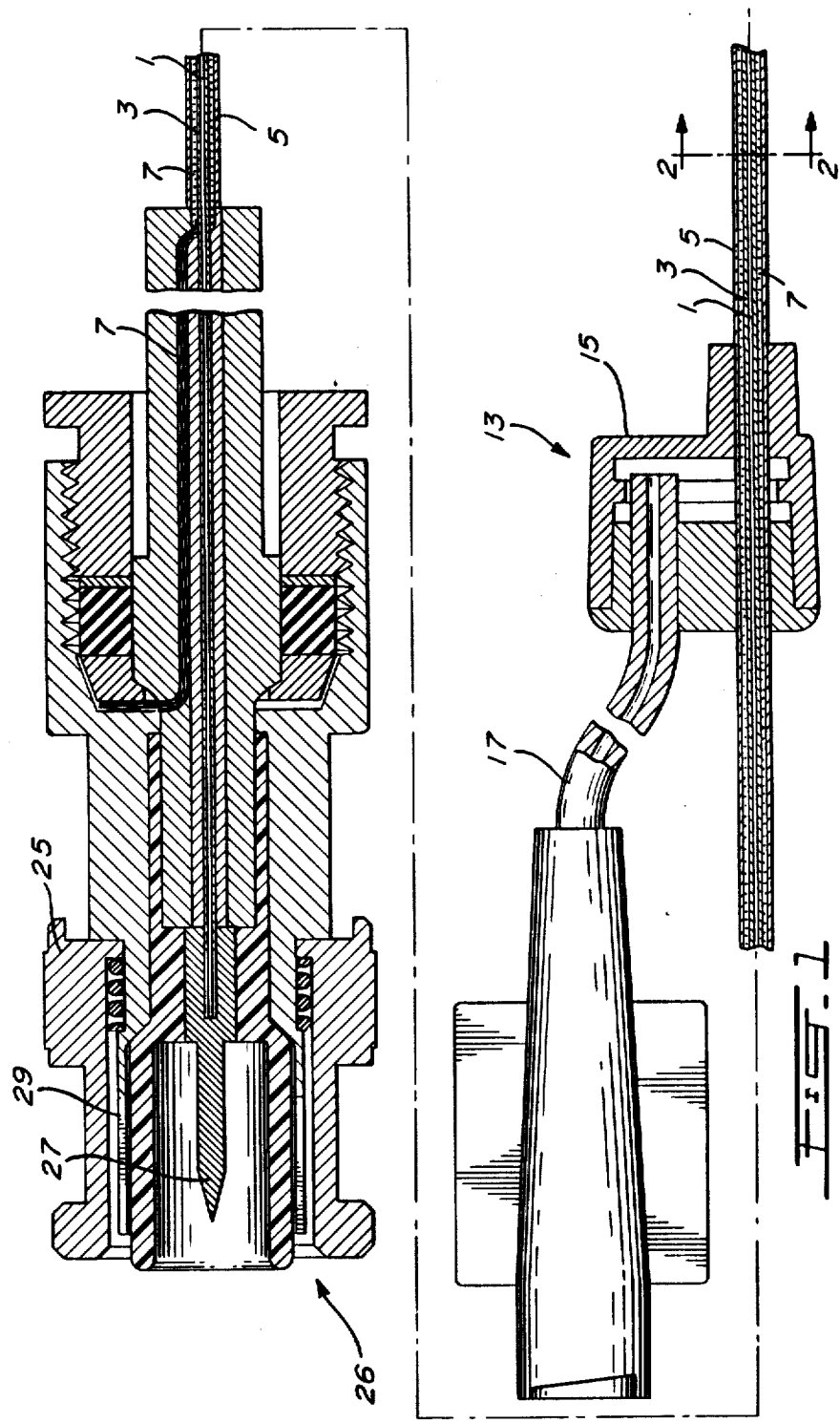

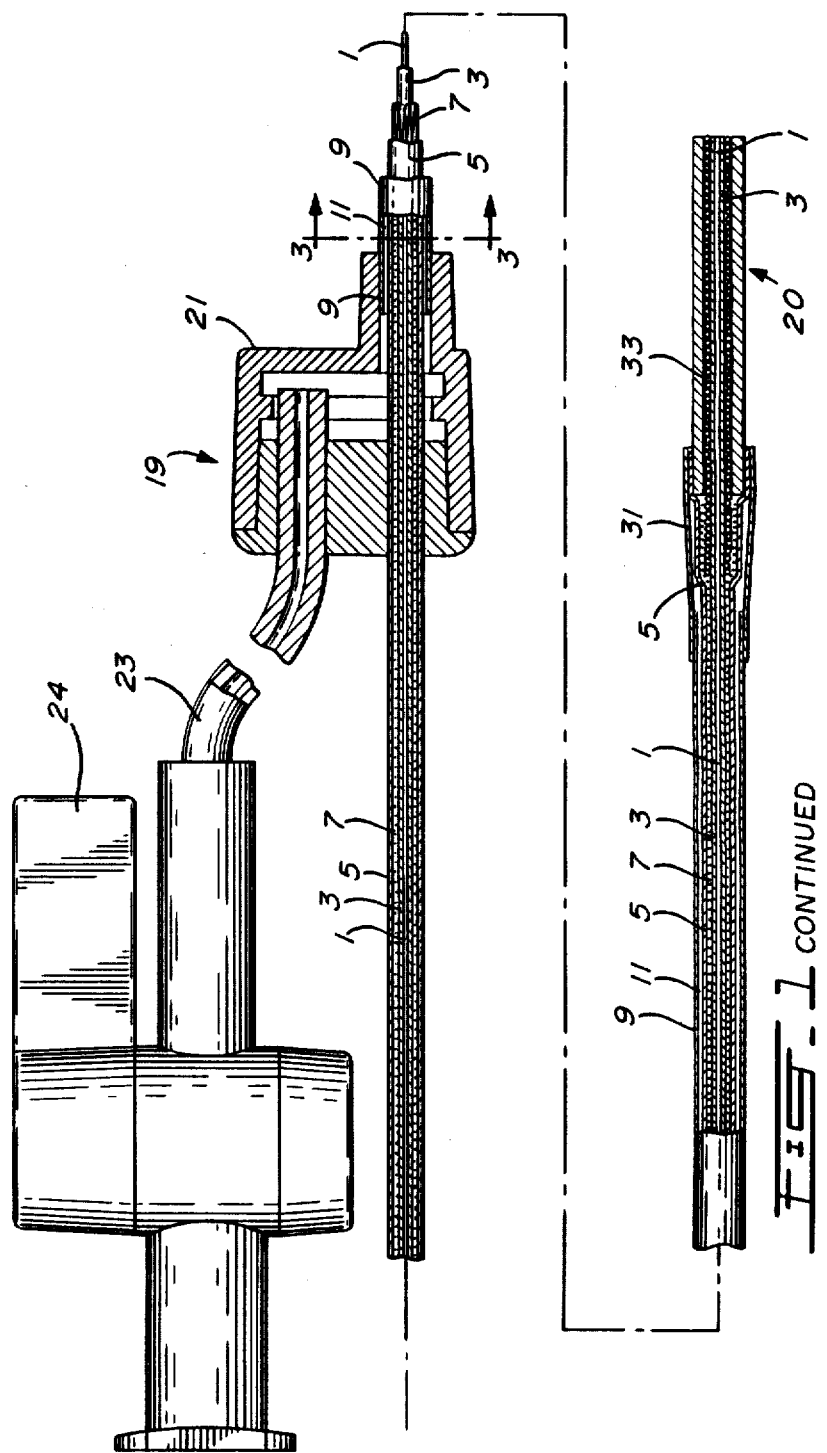

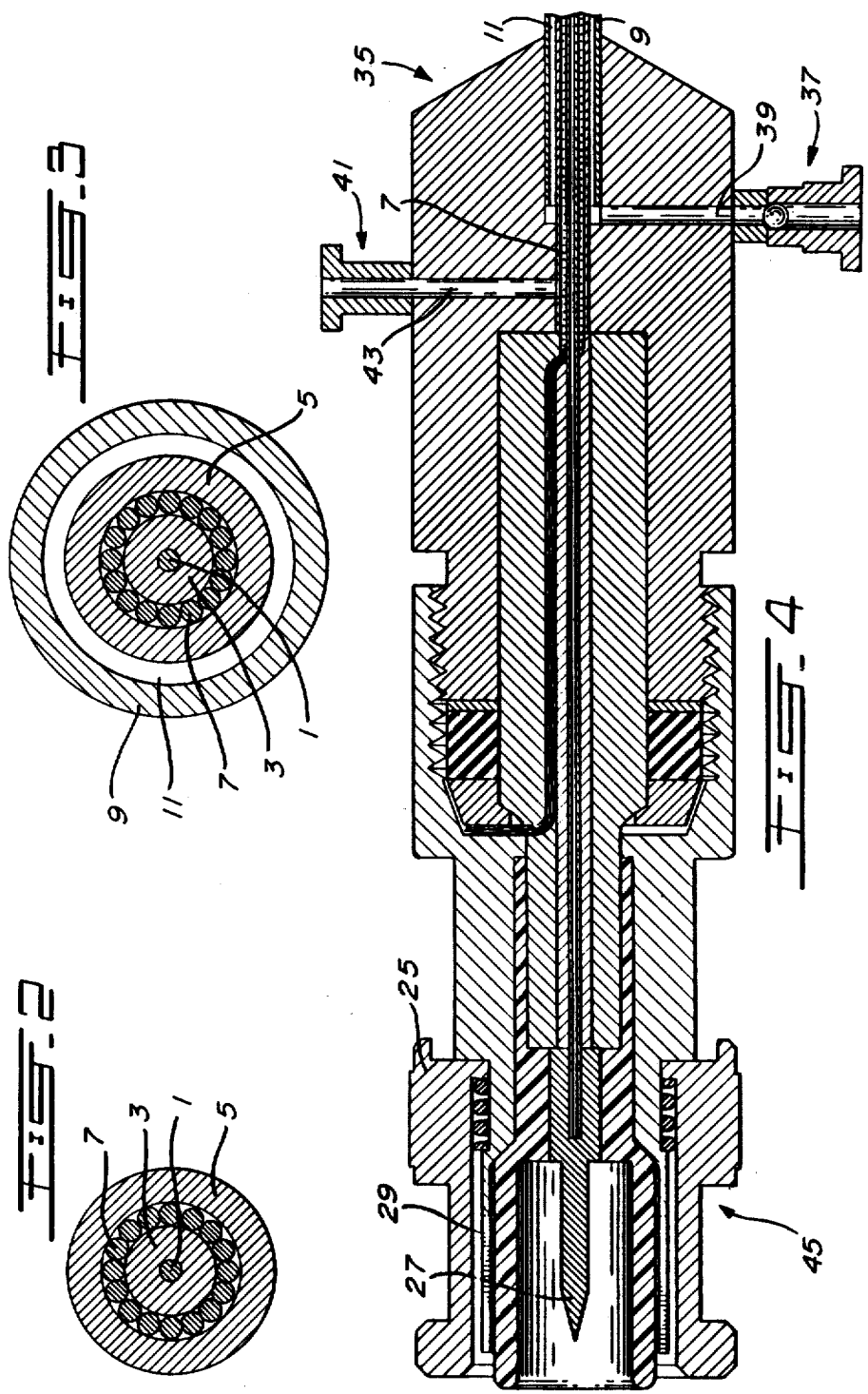

ELECTRODE FOR FIBER OPTIC SCOPES

BACKGROUND OF INVENTION

1. Field of the Invention

The invention relates to an electrode for use in fiber optic scopes. More specifically, the invention relates to such an electrode which includes an irrigant conduit integral therewith. The invention also relates to such an electrode which further includes a means for centering the electrode in a duct.

2. Description of Prior Art

Fiber optic scopes, such as nephroscopes, ureteroscopes, cystoscopes and endoscopes are used basically to provide access to cavities and ducts in the human body thereby reducing the need for surgical procedures. The electrodes are passed through the fiber optic scopes to create hydraulic shock waves which fragment the calculi.

Endourological procedures are used to remove such calculi from the kidney and ureter. In such procedures using fiber optic scopes, it is necessary to supply irrigant in the area of the calculi and the discharge end of the electrode both for the purpose of providing an electrical path between the hot and cold points of the electrode, and to carry the hydraulic shock waves. Under present procedures, irrigant is first supplied in the area through the operative channel of the scope, and the electrode is then inserted. If further irrigant is required, it is necessary to remove the electrode to provide irrigant through the operative channel. The electrode is once again inserted.

As will be appreciated, these steps increase the total time for the calculi eliminated procedure. In addition, the removal and reinsertion of instruments and electrodes is undesirable and should be kept to a minimum.

Fiber optic scopes are also used to eliminate calculi from ducts in the human body, e.g., the common duct. In procedures of this nature, for example, endoscopy, it is desirable to be able to center the electrode in the duct adjacent to the calculi. Presently available electrodes do not have any facilities for effecting this desirable end.

SUMMARY OF INVENTION

It is therefore an object of the invention to provide an electrode for fiber optic scopes which overcomes the deficiencies of the prior art.

It is a more specific object of the invention to provide such an electrode which includes an irrigant conduit integral therewith.

It is a further object of the invention to provide an electrode which includes means for centering the electrode in a duct.

In accordance with the invention there is provided an electrode for use in fiber optic scopes having a connecting end and a discharge end and including an elongated flexible center conductor and an inner insulation sleeve extending along and covering the conductor. An outer insulation sleeve extends along and covers the inner insulation sleeve and leaves a gap therebetween to define an irrigant conduit between the inner and outer insulation sleeves. A metallic sleeve extends along the irrigant conduit, the metallic sleeve being of a woven braided material whereby to permit passage of the irrigant through the irrigant conduit. Irrigant input means are in communication with the irrigant conduit.

BRIEF DESCRIPTION OF DRAWINGS

The invention will be better understood by an examination of the following description, together with the accompanying drawings, in which:

FIG. 1 is a cross-section of an electrode in accordance with the invention;

FIG. 2 is a cross-section through II—II of FIG. 1;

FIG. 3 is a cross-section through III—III of FIG. 1; and

FIG. 4 illustrates a unitary connector embodiment of the invention.

DESCRIPTION OF PREFERRED EMBODIMENTS

Referring now to the drawings, an electrode in accordance with the invention comprises an elongated flexible center conductor 1 which may be a copper wire. The copper wire is covered by an inner insulation sleeve 3 which extends along and fully covers the conductor. The outer diameter of the insulator and the wire could be of the order of 0.019 inch and the thickness of the inner insulator, which may be made of the material tefzel, could be of the order of 4.5 mil.

Outer insulation sleeve 5 covers and extends along the inner insulation sleeve and leaves a gap therebetween to define an irrigant conduit. In the gap between the insulation sleeves is a metallic sleeve 7 which comprises a woven metallic braiding. Inasmuch as the braiding is woven, and therefore includes spaces, the braiding is porous and therefore permits passage of irrigant through the space between the inner and outer insulators.

Extending along and covering the outer insulation sleeve 5 is a loosely fitting outer sheath 9. The gap 11 between the outer sheath 9 and the outer insulation sleeve 5 comprises a fluid conduit.

Irrigant inlet 13 comprises an inlet to provide irrigant to the irrigant conduit. It includes a means 15 which is in fluid contact with the irrigant conduit, and a connector 17 which is connected to a source of irrigant.

Fluid inlet 19 is in fluid communication with the fluid conduit. It includes a means 21 for effecting the fluid communication, and a connector 23 which can be connected to a source of fluid such as air. A stop cock 24 is provided at the end of the connector 23.

For electrical connection, an electrical coax connector 25 is provided at the connector end 26 of the electrode. The coax connector, as is well known in the art, includes a center pin 27 and a ground connector 29. The ground connector is, of course, an extension of the woven metallic braiding 7.

A centering means is provided at the discharge end 30 of the electrode. The centering means comprises a balloon 31, which may be of a latex material, having one end thereof attached to the outer sheath 9 and having the other end thereof attached to the outer insulation sleeve 5. The metallic braid 7 is positioned over the helical coil 33 at the discharge end 30 of the electrode, and the helix is then covered with the outer insulation sleeve 5. The helix 33 is provided both to provide memory at the discharge end of the electrode (i.e., springback) and to increase the durability thereof.

In operation, the electrode is first inserted into the human body adjacent to the calculi which is to be eliminated. Irrigant can then be supplied by connecting connector 17 to a source of irrigant and turning the source on. The irrigant will exit from the electrode at the discharge end thereof.

When the electrode is used to eliminate calculi in a duct, and it is desired to center the electrode in the duct, the connector 23 is connected to a source of fluid, for example, an air pump, and the source is turned on. This will cause the balloon to expand. The balloon will expand in such a manner that its longitudinal axis will remain coincident with the longitudinal axis of the electrode, i.e., it will evenly expand outwardly. Thus, when the balloon contacts the inner wall of a duct, the electrode will be centered in that duct. The stop cock is closed to prevent the air from escaping from the balloon after it has been inflated. Before removal of the electrode, the stop cock will be opened so that the air will be permitted to escape and the balloon will then be deflated. The air can be withdrawn from the balloon either by permitting it to escape naturally, or by applying a source of negative pressure to the connector 23.

In accordance with a further embodiment of the invention, there is provided a unitary connector for both the irrigant and the fluid inlets as illustrated in FIG. 4. As can be seen in FIG. 4, the unitary connector comprises a solid block 35. A fluid inlet 37 is connected to a fluid channel 39 which is in fluid communication with the fluid conduit 11. In a like manner, an irrigant connector 41 comprises an irrigant channel 43 which is in fluid contact with the irrigant conduit 7. In accordance with a further embodiment of the invention, the unitary connector will also include an electrical connector 45.

Although several embodiments have been illustrated, this was for the purpose of describing, but not limiting, the invention. Various modifications, which will come readily to the mind of one skilled in the art, are within the scope of the invention as defined in the appended claims.

I claim:

1. An electrode for use in fiber optic scopes, said electrode having a connecting end and a discharge end, and comprising:
    an elongated, flexible, center conductor;
    an inner insulation sleeve extending along and covering said conductor;
    an outer insulation sleeve extending along and covering said inner insulation sleeve, and leaving a gap therebetween, to define an irrigant conduit between said inner and outer insulation sleeves;
    a metallic sleeve extending along said irrigant conduit, said metallic sleeve being of a woven braided material, whereby to permit passage of said irrigant through said irrigant conduit; and
    irrigant input means in communication with said irrigant conduit.

2. An electrode as defined in claim 1 and including means adjacent the discharge end thereof for centering said electrode in a duct.

3. An electrode as defined in claim 2 and further including a loosely fitting outer sheath extending along a fluid conduit between said outer insulation sleeve and defining a fluid conduit between said outer insulation sleeve and said outer sheath;
    balloon means adjacent the discharge end of said electrode;
    said balloon means comprising said means for centering.

4. An electrode as defined in claim 3 wherein said balloon means is secured, at one end thereof, to said outer sheath, and, at the other end thereof, to said outer insulation sleeve.

5. An electrode as defined in claim 4 and further comprising fluid input means in fluid communication with said fluid conduit.

6. An electrode as defined in claim 1 and further including a metallic helix, said metallic sleeve extending along and covering said metallic helix, at said discharge end of said electrode.

7. An electrode as defined in claim 5 and further including a metallic helix, said metallic sleeve extending along and covering said metallic helix, at said discharge end of said electrode.

8. An electrode as defined in claim 1 wherein said irrigant input means comprises means in fluid communication with said irrigant conduit and connector means for connecting said input means to a source of irrigant.

9. An electrode as defined in claim 5 wherein said irrigant input means comprises means in fluid communication with said irrigant conduit and connector means for connecting said input means to a source of irrigant; and
    wherein said fluid input means comprises means in fluid communication with said fluid conduit and a connector for connecting said fluid input to a source of fluid.

10. An electrode as defined in claim 9 wherein said irrigant input means and said fluid input means comprise a single unitary connector.

11. An electrode as defined in claim 1 and including a coaxial electrical connector at the connecting end thereof, said coaxial connector including a center pin and a ground connector, said center conductor being connected to said center pin and said metallic sleeve being connected to said ground connector.

12. An electrode as defined in claim 11 wherein said irrigant input means, said fluid input means, and said coaxial connector comprise a single unitary connector.

* * * * *

UNITED STATES PATENT AND TRADEMARK OFFICE
CERTIFICATE OF CORRECTION

PATENT NO. : 4,606,331
DATED : August 19, 1986
INVENTOR(S) : William R. Shene

It is certified that error appears in the above-identified patent and that said Letters Patent is hereby corrected as shown below:

In column 4, line 6, delete "a fluid conduit between" and insert in place thereof --and covering--.

Signed and Sealed this

Fourteenth Day of June, 1988

Attest:

DONALD J. QUIGG

*Attesting Officer*  *Commissioner of Patents and Trademarks*